United States Patent
Tokuda et al.

(10) Patent No.: US 9,237,744 B2
(45) Date of Patent: Jan. 19, 2016

(54) PRESERVATIVE SOLUTION FOR CELLS, TISSUES AND ORGANS CONTAINING RARE SUGAR AND PRESERVATIVE METHOD THEREOF

(75) Inventors: Masaaki Tokuda, Kagawa (JP); Masaaki Ueki, Kagawa (JP); Rikiya Taoka, Kagawa (JP); Yoshiyuki Kakehi, Kagawa (JP); Ken Izumori, Kagawa (JP)

(73) Assignees: NATIONAL UNIVERSITY CORPORATION KAGAWA UNIVERSITY, Kagawa (JP); MATSUTANI CHEMICAL INDUSTRY CO., LTD., Hyogo (JP)

( * ) Notice: Subject to any disclaimer, the term of this patent is extended or adjusted under 35 U.S.C. 154(b) by 2551 days.

(21) Appl. No.: 11/569,577

(22) PCT Filed: May 26, 2005

(86) PCT No.: PCT/JP2005/009691
§ 371 (c)(1),
(2), (4) Date: Jul. 7, 2008

(87) PCT Pub. No.: WO2005/115141
PCT Pub. Date: Dec. 8, 2005

(65) Prior Publication Data
US 2008/0299535 A1    Dec. 4, 2008

(30) Foreign Application Priority Data
May 26, 2004 (JP) .................................. 2004-155901

(51) Int. Cl.
*A01N 1/02* (2006.01)
(52) U.S. Cl.
CPC ................ *A01N 1/0221* (2013.01); *A01N 1/02* (2013.01)
(58) Field of Classification Search
CPC ........ A23L 1/09; A23L 1/30; A61K 31/7004; A61K 8/60; A61Q 19/00; A01N 1/02; A01N 1/0221
See application file for complete search history.

(56) References Cited

U.S. PATENT DOCUMENTS

| | | | |
|---|---|---|---|
| 5,574,019 A * | 11/1996 | Segall et al. ..................... 514/23 |
| 6,176,089 B1 * | 1/2001 | Bouche ............................. 62/64 |
| 6,355,409 B1 | 3/2002 | Boelsterli |
| 6,680,305 B1 * | 1/2004 | Segall et al. .................... 514/54 |
| 7,906,487 B2 * | 3/2011 | Izumori et al. .................. 514/23 |
| 2002/0193350 A1 * | 12/2002 | Ellington et al. ............. 514/100 |
| 2004/0018482 A1 * | 1/2004 | Bronshtein ....................... 435/2 |

FOREIGN PATENT DOCUMENTS

| | | | |
|---|---|---|---|
| WO | 99 22746 | * | 5/1999 |
| WO | 00 32042 | * | 6/2000 |
| WO | WO 2002/019820 A1 | | 3/2002 |

OTHER PUBLICATIONS

K. F. Redway, "Effect of Carbohydrates and Related Compounds on the Long-Term Preservation of Freeze-Dried Bacteria", Cryobiology, vol. 11, 1987, pp. 73-79. Cited in the Intl. Search Report.
International Search Report of PCT/JP2005/009691, date of mailing Sep. 13, 2005.

* cited by examiner

*Primary Examiner* — Debbie K Ware
(74) *Attorney, Agent, or Firm* — Westerman, Hattori, Daniels & Adrian, LLP

(57) ABSTRACT

A preservative solution for low temperature preservation of animal or human organs and animal or plant tissues or cells contains D-allose. For the human kidney, cells derived from animals or humans, or human or animal sperm and/or ovum and/or fermented ovum, the preservation is conducted at from −5 to 20° C. For cells derived from animals or humans, or human or animal sperm and/or ovum and/or fermented ovum, the preservation is conducted at a temperature at which to start freezing to −196° C. A method for the low temperature preservation of an animal or human organ and an animal or plant tissue or cell at a low temperature comprises (a) refluxing or immersing a preservative solution containing D-allose and the organ or the tissue or mixing the cell therewith, and (b) cooling the organ, the tissue or the cell to a low temperature of from −5 to 20° C.

11 Claims, 11 Drawing Sheets

| | | | | |
|---|---|---|---|---|
| Tris | 2.4g | | solution A | 600ml |
| NaCl | 5.8g | | yolk | 250ml |
| KCl | 0.4g | | glycerin | 150ml |
| MgSO4 | 0.1g | | Centrifugation is conducted at 6,000 rpm for 30 min to remove unnecessary matters. | |
| Na2HPO4 | 0.05g | glycerin | | |
| NaHCO3 | 2.6g | | | |
| glucose | 17.8g | ⟶ | Glucose is replaced with D-allose. | |
| glycine | 10.0g | | | |
| calcium lactate | 0.76g | | | |
| Pluronic F-68 | 1.0g | | | |
| distilled water | 1.000ml | pH is adjusted to 7.4 with 1N HCl to form solution A. | | |

Analysis of movement rate of frozen and thawed sperm/movement rate of sperm before freezing D-allose only (A) vs D-glucose only (E) : p=0.0469 (Mann-Whitney U-test)

Analysis of movement rate of frozen and thawed sperm/movement rate of sperm before freezing No statistically significant difference among groups as measured by Tukey-Kramer test

PRESERVATIVE SOLUTION FOR CELLS, TISSUES AND ORGANS CONTAINING RARE SUGAR AND PRESERVATIVE METHOD THEREOF

CROSS-REFERENCE TO RELATED APPLICATIONS

This is a 371 of International Application No. PCT/JP2005/009691, filed May 26, 2005, which claims the benefit of priority from Japanese Patent Application No. 2004-155901, filed May 26, 2004, the entire contents of which are incorporated herein by references.

TECHNICAL FIELD

The present invention relates to a preservative solution which enables prolonged preservation of animal or human organs and animal or plant tissues or cells by low temperature preservation with a rare sugar D-allose and which is commercially practicable and effective, and a preservation method using the solution.

BACKGROUND ART

Clinical transplantation therapy of human organs such as the lung, heart, liver, kidney and pancreas has been already practiced and conducted routinely. However, a problem of lack of donors for patients waiting for transplantation who have increased year by year has become serious, and a time to wait till operation has been extended. Even though donors of organ transplantation appear, long-term preservation or supply system of blood or the like has not been currently established well.

Especially in the organ transplantation, the low temperature preservation is mainly conducted, and a time limit of preservation is approximately 4 to 24 hours. Accordingly, urgent establishment of preservation and revival techniques has been in demand. Actually, in the low temperature preservation and revival of the heart extracted from a rat, a rabbit or a baboon using University of Wisconsin Solution (UW solution), the time limit is 6 to 18 hours. In the successful transplantation of the rat's heart by preservation with a combination of this UW solution and a perfluorocarbon medium, the time limit is 24 hours (all of five rats) to 48 hours (four of five rats). The reason is that when the extracted heart is exposed to a low temperature of 4° C. or ischemic disorder, a cell membrane is damaged and thus tissue cells cannot be revived.

When an organ of a patient is seriously damaged and recovery is not expected by ordinary treatment, organ transplantation is conducted which is therapy by transplanting an organ of a donor in a recipient. A donor includes a living person and a dead person, and a dead donor includes a dead person by heart death and a dead person by cerebral death. Under the existing law ("Law regarding Organ Transplantation" effective on Oct. 16, 1997), a declaration of intention of a donor himself is required for organ extraction in both cases. In Japan with life and death thought based on Buddhism thought, donors who make a declaration of intention as an organ donor before death are quite few, and the number of donors is overwhelmingly small in comparison with the number of recipients.

When an organ is extracted from a living body or a donor is dead, its viability is rapidly lost. When an organ poor in viability is transplanted, it is destroyed within a body of a recipient without exhibiting the predetermined function despite good histocompatibility of the organ. Accordingly, apart from the problem of the histocompatibility, it is no exaggeration to say that whether or not organ transplantation is successful depends on how a time that lapses from extraction of an organ to transplantation thereof can be shortened. Since donors are now very few, there is a rare case that a donor resides near a recipient. Therefore, in a site of organ transplantation, an information on donors has been often exchanged usually, or a time that lapses from extraction of an organ to transplantation thereof has been shortened as much as possible by transporting an extracted organ via a helicopter or a jet. However, it is quite clear that such a method depending on a transportation time is limited. For overcoming this limitation, diverse preservative agents for low temperature preservation of organs have been contrived.

As an organ preservative agent which has been put to practical use, an EuroCollins solution comprising glucose and various electrolytes and a UW solution comprising an impermeable component, an oncotic pressure component, an energy metabolism acceleration component and hormone have been well known. It has been said that the EuroCollins solution is effective for the kidney having high viability, while an effect of protection for tissues and cells other than the kidney is not satisfactory. Further, it has been said that the UW solution has defects that it is unstable as a pharmaceutical preparation and has to be preserved at a low temperature after formulation.

As an organ preservative agent free from such detects, Patent Document 1 proposes an organ preservative agent comprising trehalose, hydroxyethyl starch and various electrolytes, and Patent Documents 2 to 4 propose an organ preservative agent comprising potassium L-ascorbic acid DL-α-tocopherol phosphoric acid diester (hereinafter abbreviated as "EPC-K") as a synthetic substance. However, the former organ preservative agent involves problems that since the molecular weight and the degree of substitution of the hydroxyethyl starch as a synthetic substance have to be adjusted to quite limited ranges, it is difficult to formulate the pharmaceutical preparation and maintain homeostasis. Since EPC-K used in the latter organ preservative agent is low in solubility in water and has various pharmacological activities, the mixing amount of EPC-K has to be decreased or the use of the agent itself has to be abandoned sometimes for reasons of recipients.

Patent Document 1: gazette of JP-A-6-40801
Patent Document 2: gazette of JP-A-6-166624
Patent Document 3: gazette of JP-A-7-215801
Patent Document 4: gazette of JP-A-7-330501

DISCLOSURE OF THE INVENTION

Problems that the Invention is to Solve

Transplantation of organs such as the kidney, liver, heart, lung, pancreas and intestines has been currently utilized. In repair, a transplanted organ is washed out with a preservative solution through its vasculacture. This solution is designed to make easy the adjustment of a temperature of an organ, prevent expansion of cells, remove a free oxygen group, control pH, decrease ischemic damage and increase a safe period of time. Accordingly, an organ can be preserved outside the body, and repair of the organ can be accelerated by reperfusion. A significant preservative solution was introduced by Belzer in 1967 and by Collins in 1969, and was thereafter improved by EuroCollins (EC), Marshall (1976) and Brettschneider (refer to Izmer et al. in 1998). Among all of the solutions, the University of Wisconsin solution (UW solution) which was most successful was introduced by Belzer and his colleagues in 1988. However, it is clear that high-quality transplantation directly leads to improvement in function, prolonging the functional transplantation life. Thus, necessity for improving the preservative solution is said to still remain.

Meanwhile, 10% to 15% of couples hoping to have a child are sterile, and recent introduction of assisted reproductive technology (ART) makes it possible for couples so far considered absolutely sterile to have a child, and it helps to improve QOL of patients. When a man in reproductive age experiences anticancer chemotherapy or orchidectomy, a case of practicing long-term freeze-preservation for hoping to have a child in future has been increased. Thus, the further improvement in preservative solution has been in demand. Likewise, a procedure of recovering unfertilized ova and freeze-preserving the same has been also conducted, when fertilization does not occur between a sperm and an ovum in good timing for some reasons or therapy such as radioactive therapy or chemotherapy is considered to affect an ovarian tissue to decrease the number of ova. Moreover, freeze-preservation of fermented ova has been conducted.

A large number of researchers have tried to develop an improved solution and a relatively simple solution containing many additives. Since quite a wide variety of conditions are included in differing organs, it is clearly unreasonable to aim to obtain a single universal preservative solution. However, the present inventors aim to search essential components which form basis for a preservative solution appropriate for a specific organ (kidney) and to prove by experiments that the preservative solution can be a single universal preservative solution.

Specifically, the invention aims to (1) prove experimentally that the UW solution can be improved as a preservative solution appropriate for a specific organ (kidney) using D-allose. Further, it aims to provide (2) a preservative solution to enable prolonged preservation of animal or human organs and animal or plant tissues or cells by low temperature preservation (from −5 to 20° C.) and which is commercially practicable and effective, and (3) a preservative solution to enable prolonged preservation of animal or human organs and animal or plant tissues or cells by low temperature preservation (from a temperature at which to start freezing to −196° C.) and which is commercially practicable and effective.

In addition, (4) a report stating that oxidative stress causes functional abnormality of sperm or ovum has been lately seen in various documents, and the invention aims to improve a low temperature preservation solution or a freeze-preservative solution of sperm and/or ovum and/or fermented ovum using rare sugars (among rare sugars, D-allose having an antioxidation activity).

Means for Solving the Problems

The subject matter of the invention is a preservative solution for low temperature preservation of animal or human organs and animal or plant tissues or cells as described in (1) to (8) below.

(1) A preservative solution for low temperature preservation of animal or human organs and animal or plant tissues or cells, the solution containing a rare sugar, preferably D-allose.

(2) The preservative solution for low temperature preservation of animal or human organs and animal or plant tissues or cells according to the above (1), wherein the low temperature preservation is conducted at from −5 to 20° C.

(3) The preservative solution of the above (2), which is a preservative solution for low temperature preservation of the human kidney.

(4) The preservative solution of the above (2), which is a preservative solution for low temperature preservation of cells derived from animals or humans.

(5) The preservative solution of the above (4), which is a preservative solution for low temperature preservation of human or animal sperm and/or ovum and/or fermented ovum.

(6) The preservative solution for low temperature preservation of animal or human organs and animal or plant tissues or cells according to the above (1), wherein the low temperature preservation is conducted at a temperature of from a temperature at which to start freezing to −196° C.

(7) The preservative solution of the above (6), which is a preservative solution for low temperature preservation of cells derived from animals or humans.

(8) The preservative solution of the above (7), which is a preservative solution for low temperature preservation of human or animal sperm and/or ovum and/or fermented ovum.

The subject matter of the invention is a method for low temperature preservation of animal or human organs and animal or plant tissues or cells as described in (9) to (12) below.

(9) A method for low temperature preservation of an animal or human organ and an animal or plant tissue or cell at a low temperature, which comprises (a) refluxing or immersing a preservative solution for low temperature preservation containing a rare sugar, preferably D-allose and the organ or the tissue or mixing the cell therewith, and (b) cooling the organ, the tissue or the cell to a low temperature of from −5 to 20° C.

(10) A method for low temperature preservation of human or animal sperm and/or ovum and/or fermented ovum at a low temperature, which comprises (a) mixing a preservative solution for low temperature preservation containing a rare sugar, preferably D-allose with the sperm and/or ovum and/or fermented ovum, and (b) cooling the cell to a low temperature of from −5 to 20° C.

(11) A method for low temperature preservation of an animal or human cell at a low temperature, which comprises (a) refluxing or immersing a preservative solution for low temperature preservation containing a rare sugar, preferably D-allose and the organ or the tissue or mixing the cell therewith, and (b) cooling the organ, the tissue or the cell to a low temperature of from a temperature at which to start freezing to −196° C.

(12) A method for low temperature preservation of human or animal sperm and/or ovum and/or fermented ovum at a low temperature, which comprises (a) mixing a preservative solution for low temperature preservation containing a rare sugar, preferably D-allose with the sperm and/or ovum and/or fermented ovum, and (b) cooling the cell to a low temperature of from a temperature at which to start freezing to −196° C.

Advantage of the Invention

1) The UW solution containing D-allose can be improved as a preservative solution appropriate for the kidney.

2) A preservative solution can be provided which enables prolonged preservation of animal or human organs and animal or plant tissues or cells by low temperature preservation (from −5 to 20° C.) and which is commercial practicable and effective.

3) A preservative solution can be provided which enables prolonged preservation of animal or human organs and animal or plant tissues or cells by low temperature preservation (from a temperature at which to start freezing to −196° C.) and which is commercially practicable and effective.

4) Recently, a report stating that oxidative stress causes functional abnormality of sperm or ovum has been seen in various documents, and the invention can provide a low temperature preservation solution or a freeze-preservative solution which improves a survival rate of sperm and/or ovum and/or fermented ovum and a movement rate of sperm using rare sugars (especially D-allose) having an antioxidation activity, and a method for preservation using these solutions.

BEST MODE FOR CARRYING OUT THE INVENTION

The rare sugars, preferably D-allose used in the invention will be described below. The "rare sugars" can be defined as monosaccharides which are present in the natural world only in small quantities. Monosaccharides which are present in the natural world in large quantities are seven types, D-glucose, D-fructose, D-galactose, D-mannose, D-ribose, D-xylose and L-arabinose. Other monosaccharides are present in the natural world in small quantities, and classified into rare sugars. Polyols are formed by reducing monosaccharides, and D-sorbitol and D-mannitol are present in the natural world in relatively large quantities. However, other sugar alcohols are present in small quantities. Therefore, these are defined as rare sugars according to the invention. These rare sugars have been so far hardly procured. However, a method for producing rare sugars from monosaccharides present in the natural world in large quantities is being developed, and rare sugars can be produced by this technique.

The monosaccharides are further described below by referring to Izumoring (registered trademark, hereinafter omitted) proposed for facilitating the understanding of the relation of these monosaccharides (refer to WO 03/097820).

A link view in which all of monosaccharides having from 4 to 6 carbon atoms are linked according to a production process and molecular structures (D-form and L-form) as shown in FIG. 17 is an overall view of Izumoring. That is, what is understandable from FIG. 17 is that all of monosaccharides having 4, 5 and 6 carbon atoms are linked. In the overall view, there are a link in Izumoring C6, a link in Izumoring C5 and a link in Izumoring C4, and C4, C5 and C6 are all linked. This idea is important. For decreasing the carbon number, a fermentation method is mainly used. The view is also characterized in that it is a great link view in which all of the monosaccharides different in carbon number are linked.

In Izumoring of monosaccharide having 6 carbon atoms (hexose), as shown in a lower portion of FIG. 18 and FIG. 19, monosaccharide having 6 carbon atoms (hexose) includes in total 34 types, aldose 16 types, ketose 8 types, and polyol 10 types respectively. It has been known by studies including studies of the present inventors that these sugars can be converted by a reaction with an oxidoreductases, a reaction with an aldose isomerase or a reaction with an aldose reductases.

In the past studies, however, the upper group, the middle group and the lower group were not linked by an enzyme reaction. That is, D-glucose or D-fructose belonging to the upper group is a sugar present in the natural world in large quantities, and less costly, but rare sugars could not be synthesized from these. However, during the studies of the present inventors, an enzyme by which to link them was discovered. It starts from the fact that entirely unexpected D-sorbose was discovered in a culture solution of a microorganism containing an enzyme by which to synthesize D-tagatose from galactose. As a result of examining the cause thereof, it has been found that this microorganism produces an enzyme called D-tagatose 3 epimerase (DTE).

As shown in the lower portion of FIG. 18 and FIG. 19, this DTE is found to be an enzyme by which to link D-tagatose and D-sorbose which has been disconnected so far. Further surprisingly, it has been found that this DTE is an enzyme that catalyzes epimerization of the 3-position of all ketoses and is a unique enzyme having quite a wide substrate specificity that it acts on D-fructose and D-psicose, L-sorbose and L-tagatose, D-tagatose and D-sorbose, and L-psicose and L-fructose which have not been synthetically connected so far. By the discovery of this DTE, all of the monosaccharides have been linked in a ring mode, and the knowledge of monosaccharides has been completely systematized. It has been designated Izumoring.

A close look at FIG. 19 reveals that L-form is on the left side, D-form on the right side and DL-form in the middle and L-form and D-form are symmetric about the center (star) of the ring. For example, D-glucose and L-glucose are in point symmetry about the central point. Besides, the value of Izumoring is that this view is also a design view for production of all monosaccharides. In the above example, when L-glucose is produced starting from D-glucose, D-glucose is subjected to isomerization→epimerization→reduction→oxidation→epimerization→isomerization to form L-glucose.

A relation between sugars present in the natural world in large quantities and rare sugars present therein in small quantities is shown using Izumoring of monosaccharide having 6 carbon atoms (hexose). D-glucose, D-fructose, D-mannose and D-galactose which can be produced from lactose in milk are present in the natural world in large quantities, and other sugars are classified as rare sugars present in small quantities. The discovery of DTE has made it possible to produce D-fructose and D-psicose from D-glucose and further D-allose, allitol and D-talitol therefrom.

To sum up the meanings of Izumoring of monosaccharide having 6 carbon atoms (hexose), all of monosaccharides are structurally arranged according to a production process and molecular structures (D-form and L-form) (systematization of knowledge) to be able to grasp the whole image of monosaccharides, an effective and efficient approach of studies can be selected, an optimum production route can be designed, and a defective portion can be foreseen.

D-allose is described below. D-allose is a rare sugar which has been found to have various physiological activities in particular during studies of rare sugars. D-allose (D-allohexose) is a D-isomer of allose classified into aldose (aldohexose), and it is hexose ($C_6H_{12}O_6$) having a melting point of 178° C. A process for producing this D-allose includes a process in which D-allonic acid lactone is reduced with sodium amalgam and a process in which D-allose is formed from D-psicose using L-rhamnose isomerase as described in Shakewat Hosein Puiyan et al. "Journal of Fermentation and Bioengineering" vol. 85, pp. 539-541 (1993). Further, in recent years, a process in which D-allose is formed from D-psicose by reacting a solution containing D-psicose with D-xylose isomerase has been invented as described in JP-A-2002-17392. According to the process described in JP-A-2002-17392, in the formation of D-allose, it is obtained as an enzyme reaction solution containing newly formed D-allose together with unreacted D-psicose.

Although the type of the enzyme used to convert a substrate convertible to D-allose to D-allose by an enzyme reaction is not limited, an enzyme "L-rhamnose isomerase" by which D-allose can be produced from D-psicose is shown as a preferable enzyme. L-rhamnose isomerase is a known enzyme which was made public in "Journal of Fermentation and Bioengineering" vol. 85, pp. 539-541 (1998). It is an enzyme that catalyzes an isomerization reaction from L-rhamnose to L-rhamnulose and an isomerization reaction from L-rhamnulose to L-rhamnose. Since L-rhamnose isomerase also acts on isomerization between D-allose and D-psicose, it is an enzyme that can catalyze production of D-allose from D-psicose.

The preservative solution of the invention may be in the form of a rare sugar D-allose alone or in the form of a composition of the rare sugar D-allose and one or more selected from components which are generally incorporated in organ preservative agents, for example, saccharides other than the rare sugar D-allose, such as glucose, maltose, sucrose, lactose, raffinose, trehalose, mannitol, hydroxyethyl starch and pullulan, organic acids such as gluconic acid, lactic acid, acetic acid, propionic acid, β-hydroxybutyric acid and citric acid, electrolytes such as sodium chloride, potassium chloride, magnesium chloride, calcium chloride, sodium dihydrogenphosphate, potassium dihydrogenphosphate, disodium hydrogenphosphate, dipotassium hydrogenphosphate, sodium hydrogencarbonate, potassium hydrogencarbonate, sodium carbonate and potassium carbonate, vitamins such as L-ascorbic acid and vitamin E, amino acids such as glycine, glutamic acid and lysine, hormones such as antidiuretic hormone and insulin, anticoagulants such as citric acid, citrate, heparin and disodium edetate, antihypertensive agents such as a calcium antagonist, an adrenaline β-receptor antagonist and an angiotension converting enzyme inhibitor, nucleic acid bases such as adenosine acid phosphate, antifreezing agents such as an antifreezing protein (hereinafter referred to as "AFP"), active oxygen eliminators, cell activators, antibiotics, antiplatelet factors, hepatopathy inhibitors, excipients, binders, disintegrants, dispersing agents, viscous agents, reabsorption accelerators, surfactants, solubilizing agents, preservatives, antiseptics, emulsifying agents, isotonic agents, stabilizers, buffers and pH adjustors.

The preservative solution of the invention is usually prepared in the form of a liquid preparation. It may be prepared, as required, in the form of a solid preparation such as a powder, granules, tablets or capsules. The solid preparation can be used by being dissolved, suspended or emulsified in an aqueous medium such as purified water, distilled water for injection, sterile purified water, a physiological saline solution or a mixed solution of any of these and a hydrophilic organic solvent. When D-allose used in the preservative solution of the invention is incorporated into the known organ preservative solution such as the EuroCollins solution or the UW solution, the organ preservability thereof can be improved. Although the mixing amount of the rare sugar D-allose in the preservative solution of the invention varies with the use and the dosage form, it is usually 0.0001% (w/w) or more, preferably 0.001% (w/w) or more.

A use method of the preservative solution in the invention is described.

The preservative solution of the invention can be used similarly to a known preservative solution for animal or human organs and animal or plant tissues or cells. When it is used as a preservative solution for organs, so-called "simple freeze-preservation method" and "low-temperature continuous perfusion-preservation method" can be applied in combination with a known organ preservation container or a known perfusion device. For example, it can be used as an initial perfusion solution of an organ immediately after extraction, an immersion preservative solution and a perfusion preservative solution after initial perfusion or a rinse solution before reperfusion of blood. An osmotic pressure in immersion or perfusion of an organ may be set at a range of from 250 to 500 mOsm/l, preferably from 300 to 450 mOsm/l, and pH at a range of from 3 to 10, preferably from 6.5 to 8.0 respectively. A concentration of the rare sugar D-allose in use is in the range of, usually 0.01 mM or more, preferably from 0.1 to 200 mM. Accordingly, in some form of the preservative solution for organs, it is properly dissolved or diluted before use such that the concentration is adjusted to the foregoing range. Although a temperature at which the organ is immersed or immersed and preserved varies with the type of the organ, the condition in extraction and the preservation time, it is set at, usually a temperature less than a body temperature, preferably from −5 to 20° C., more preferably from −3 to 15° C.

Human sperms are manually collected after abstinence for from 3 to 5 days. Sperms are sterically separated from the collected semen, and then mixed with the preservative solution of the invention. The mixture is quickly preserved in liquid nitrogen. Ova separated from the ovary are mixed with the preservative solution of the invention, and quickly preserved in liquid nitrogen.

Examples of animal or human organs and animal or plant tissues or cells in the invention include tissues outside the living body of animals or humans, such as a skin tissue and a mucous membrane, internal tissues of abdomen and breast, for example, digestive organs such as liver, kidney, spleen, pancreas, lung, intestines and stomach, urinary organs such as bladder, genital organs such as uterus and spermary, tissues of the brain and neck, and tissues of bones, joints, ligament, muscles, blood vessels and nerves. These are put outside the living body for use in, for example, organ transplantation. The invention aims at preservation of organs on the premise of transplantation. Accordingly, the organs referred to in the invention are not to be limited to organs in a narrow sense of the word, such as kidney, liver, pancreas, lung and heart, but include other tissues other than the foregoing organs, such as bone marrow, eyeball, cornea, bones, skins, blood vessels, valves and parathyroid glands. Further, cells also include animal cells and plant cells as well as culture cell strains. Examples of the cells include wide-ranging cells, such as blood cells, sperms, ova, various stem cells and commercially available culture cells for study. In the preservative solution for organs in the invention, whether classification of organ transplantation is genetic classification or anatomical classification does not matter. Transplantation may be genetically autotransplantation, heterotransplantation or allotransplantation, and anatomically orthotropic transplantation or heterotropic transplantation.

A cell is a functional structural unit of all organisms except viruses. The cell has a structure separated from the outside via one membrane (cell membrane), and is grown by division. An organism is classified into a unicellular organism made of a single cell and a multicellular organism made of plural cells. A human being is a multicellular organism made of approximately 70,000,000,000,000 cells. The cell has thereinside nucleus, mitochondria, Golgi apparatus, centrosomes and the like. Plant cells further contain chloroplast and developed vacuole, having a structure different from animal cells. However, it is basically similar to the animal cell. In the multicellular organism, cells are gathered to form a tissue, plural tissues are gathered to form an organ, and an assembly of plural organs forms an individual of an animal or a plant. Accordingly, a product that preserves the cells satisfactorily may be considered to have potential of preserving tissues or organs satisfactorily.

The invention is specifically illustrated below by referring to Examples. The invention is not limited by these Examples at all.

Example 1

Using culture cells, the effect of rare sugars on freeze-preservation thereof were analyzed. The survival rate of cells, and the growth rate of survived cells and the like were examined.

[Method]

1. Cells used: Hela (human cervical cancer), OVCAR-3 (human ovarian cancer), HuH-7 (human liver cancer), HaCaT (human skin keratinocyte), HFB (human fibroblast) and NIH3T3 (mouse fibroblast).

2. Freeze-preservation

Saccharides D-allose and the like were added to culture medium, Cell Banker (commercially available preservative solution) and DMSO at concentrations of 25 mM and 50 mM. Monosaccharides such as D-glucose, D-fructose, D-mannose and D-galactose which are present in nature in large quantities and D-allose, D-psicose, D-altrose, allitol, D-talitol and L-sorbose as rare sugars were used. Further, trehalose as disaccharide was used. The cells were preserved for 24 hours by being frozen at −80° C.

3. Measurement

1) Survival rate of cells: One day later, the cells were thawed, and the survival rate was estimated by trypan blue dying method.

2) Cell growth: One day later, the cells were thawed, and $0.25\sim2\times10^4$ cells/well were spread on 96-well plate with 0.1 mL medium. After a prescribed period of time, the cell growth was measured by MTT assay.

[Results]

1) The survival rate of cells frozen with culture medium alone was estimated after thawing, it was clarified that a larger number of HFB cells were survived by addition of the rare sugars (FIG. 1). The survival rate was generally high by addition of the rare sugars in comparison with that by addition of D-glucose, D-fructose, D-mannose and D-galactose present in nature in large quantities.

2) The growth of cells after thawing was examined as an experiment to look into the function of the frozen cells. Consequently, the growth rate was high in the HFB cells preserved by addition of the rare sugars such as D-allose in comparison with that in other cases and the cells were functionally undamaged (FIG. 2). In comparison with trehalose which has been often used as a cryoprotectant in documents, nearly the same effect was obtained. The same experiment was conducted using NIH3T3 cells, and the same results were obtained.

3) Then, the rare sugar was added to Cell Banker which was widely used for freeze-preservation of cells, and an effect of preservability was comparatively studied. The HFB cells and the NIH3T3 cells freeze-preserved with Cell Banker containing rare sugar were found to have a higher proliferation ability than that in case of Cell Banker alone (FIG. 3, in case of NIH3T3). In comparison with trehalose, nearly the same effect was obtained.

4) Since DMSO (dimethyl sulfoxide) is also commonly added to culture medium at a rate of 10% and used in freeze-preservation, the effect of rare sugar was examined in the system of DMSO. The difference in effect of rare sugar is hardly observed in a system using 10% DMSO, the effect of cell preservation was comparatively examined under a sub-optimal condition by decreasing the concentration of DMSO to 1%. NIH3T3, OVCAR-3, HaCaT and HFB cells and the like were used. It was confirmed that the effect of preservation with DMSO was improved by addition of D-allose (FIG. 4, in case of NIH3T3 cells; FIG. 5, in case of OVCAR-3 cells).

[Considerations]

1) Regarding the rare sugars such as D-allose, the cell preservation effect was found to be high in improvement of the survival rate in comparison with natural monosaccharides such as D-glucose. When the cell growth was thereafter examined, the growth of cells preserved in the presence of the rare sugar (D-allose) was higher than that in other cases.

2) The foregoing effect was found to be at least similar to the effect of trehalose which was reported to have an effect of cell preservation (Biol Reprod. 2003 October; 69 (4): 1245-50, Epub 2003 Jun. 11, et al.).

3) Since the addition of rare sugars such as D-allose provides the cell freeze-preservation effect, it may be possible to develop D-allose as an effective preservative agent for long-term preservation of cells or organs.

4) From now on, the past studies are continued, preservative solutions are prepared by adding various sugars to ordinary freeze-preservative solutions and stored in a freezer of −80° C. or in liquid nitrogen, and an influence on a survival rate and functions of cells is examined.

5) Effectiveness is examined by varying the type of the sugar, the concentration thereof, the combination of rare sugars and the preservation period, and optimum conditions are clarified.

Example 2

Using culture cells, the effect of rare sugar on freeze-preservation thereof was analyzed. The survival rate of cells, and the growth rate of the survived cells and the like were examined. Although examination was conducted at the low concentration of 50 mM in Example 1, the present inventors found that the preservation was more effective at a higher concentration, which was verified in this Example.

[Method]

1. Cells used: Hela (human cervical cancer), OVCAR-3 (human ovarian cancer), HaCaT (human skin keratinocyte), HFB (human fibroblast) and NIH3T3 (mouse fibroblast).

2. Freeze-Preservation

Saccharides D-allose and the like were added to culture medium, Cell Banker (commercially available preservative solution) and DMSO at concentrations of 0.2, 0.4, 0.6, 0.8 and 1M. Monosaccharides such as D-glucose, D-fructose, D-mannose and D-galactose which are present in nature in large quantities and D-allose, D-altrose, D-psicose, L-psicose, D-sorbose, L-sorbose, D-tagatose, L-tagatose and L-fructose as rare sugars were used. Further, trehalose as disaccharide was used. The cells frozen with D-allose were freeze-preserved at −80° C. and in liquid nitrogen for 24 hours, 1 week and 4 weeks.

3. Measurement

1) Survival rate of cells: The cells were thawed, and the survival rate was estimated by a trypan blue dying method.

2) Cell growth: The cells were freeze-preserved with D-allose and trehalose at optimum concentrations for 24 hours, thawed, and spread on a 96-well plate such that the concentration was $0.5\text{-}1\times10^4$ cells/well/0.1 ml. After a prescribed period of time, the cell growth was measured by MTT assay.

[Results]

1) Regarding the survival effect of the cells after thawing in the addition of D-allose to the culture medium alone, the optimum concentration of D-allose in various cells tested is 0.4~0.6 M. At this time, the survival rate of the cells was estimated to be approximately 40~70% (FIG. 6).

2) As to the cell survival rate after thawing, comparison with other rare sugars and sugars present in nature in large quantities (0, 0.2, 0.4, 0.6, 0.8 and 1M) is currently under way. There is a tendency that the survival rate of cells by addition of D-allose is the highest in comparison with that by addition of other rare sugars.

3) Cells preserved with D-allose-containing medium, Cell Banker cell preservative solution, medium only and trehalose-containing medium were subjected to trypan blue dying. Cells that look white are living cells, and cells that look black are dead cells with trypan blue incorporated. In comparison with cells preserved in the medium alone, the number of cells survived in preservation with the D-allose-containing medium was large, and it was the same as the number of cells survived with the trehalose-containing preservative solution often used in documents (FIG. 7).

4) In the experiment in which the function of the frozen cells was examined, it was found that the cells preserved by addition of D-allose were higher in growth rate than the cells in other cases and were less impaired functionally than the cells preserved with the commercially available Cell Banker cell preservative solution which is ordinarily used. When D-allose was compared with trehalose, nearly the same effect was obtained (FIG. 8).

5) D-allose was added to 10% DMSO (dimethyl sulfoxide) and Cell Banker widely used for freeze-preservation of cells, and the effect on preservability was comparatively studied. In comparison with DMSO and Cell Banker, the higher the concentration of D-allose, the lower the survival rate of cells.

6) The effect of cell preservation under sub-optimal conditions by reducing the concentration of DMSO to 1, 2 or 3% was comparatively examined. OVCAR-3, HaCaT and HDF cells were used as cells. Regarding the preservation effect with DMSO, it was confirmed that the survival rate was approximately 70% or more with the use of 1 or 2% of DMSO by addition of D-allose (FIG. 9).

7) Even though the time of freeze-preservation was extended by one month, the survival rate of cells was not changed so much.

8) Regarding the temperature of freeze-preservation, the survival rate at −80° C. was much higher than that in liquid nitrogen.

[Considerations]

1) In the foregoing studies, the concentration of D-allose was 50 mM, and no great improvement effect was obtained. For increasing the effectiveness of D-allose as a preservative agent, the optimum concentration of D-allose was 0.4~0.6 M.

2) There was a tendency that D-allose had the strong effect of cell preservation. The cells preserved in the presence of D-allose were high in growth ability of cells after thawing in comparison with the cells preserved without D-allose.

3) Through the comparative study, the foregoing effect was found to be at least similar to the effect of trehalose which was reported to have an effect on cell preservation (Biol Reprod. 2003 October; 69 (4):1245-50, Epub 2003 Jun. 11, and the like).

4) It is considered that D-allose can decrease the use amount of freeze-preservative solution DMSO that damages cells.

5) An optimum preservation temperature of a D-allose-containing freeze-preservative agent is −80° C.

6) Since the addition of rare sugars such as D-allose provides the cell freeze-preservation effect, it may be possible to develop D-allose as an effective preservative agent for long-term preservation of cells or organs.

7) From now on, the past studies are continued, an influence on a survival rate and functions of cells is examined by varying the type and the concentration of the rare sugar, the freeze-preservative solution and the like, and optimum conditions are clarified.

Example 3

Subject of experiment: Improvement of UW solution using D-allose

INTRODUCTION

An adhesion rate of the kidney after renal transplantation has been abruptly improved along with the development of the UW solution. However, ischemia of the transplanted kidney induces the acute rejection of the transplanted kidney or the decrease in function thereof which greatly influences the adhesion rate.

In the renal ischemia, ATP is depleted in the angioendothelium, and calcium and active oxygen (reactive oxygen species: ROS) are produced to activate neutrophils and express bonding factors such as ICAM-1. Further, in the blood cell system, macrophages are activated to release TNF (tumor necrosis factor) or ROS. Consequently, neutrophils are activated and accumulated with expressed bonding factors, and entered from the angioendothelium to the tissue to release histolytic enzymes such as elastase, which leads to tissue disorders. For preventing the functional disorder and the rejection of the transplanted kidney after renal transplantation, various anticytokine preparations, inhibition of bonding factors such as ICAM-1 have been attempted.

Meanwhile, growth factors such as epidermal growth factor (EGF) and hepatocyte growth factor (HGF) are involved in regeneration of uriniferous tubule cells from the ischemic renal insufficiency. It has been said that the renal disorder is inhibited and the renal recovery is accelerated by administering these growth factors after ischemia.

A kidney preservative solution having an activity of inhibiting production of detrimental factors of the kidney in the preservative solution and maintaining or increasing production of regeneration factors is improved more than ever, making it possible to prolong the kidney preservation time or reduce the rejection of the transplanted kidney and the functional disorder. Thus, the adhesion of the transplanted kidney is expected to be rapidly improved.

In the renal transplantation, the prolongation of the kidney preservation time or the reduction of the rejection of the transplanted kidney or the functional disorder is enabled by the two points, (1) the improvement of a kidney preservative solution having an activity of inhibiting production of detrimental factors of the kidney in the preservative solution and maintaining or increasing production of regeneration factors, and (2) inhibition of activation and accumulation of neutrophils that cause the tissue disorder after transplantation. It is thus expected that the adhesion of the transplanted kidney is rapidly improved.

Accordingly, this Example examined the following.

1. Effect on ICAM-1 as a leukocyte bonding factor and EGF as a regeneration factor in the kidney by addition of D-allose to the UV preservative solution. 2. Effect of D-allose on CINC-1 as an activation factor of leukocyte and accumulation (MPO) of leukocytes after renal ischemic reperfusion.

[Method]

1.

Object: male rats, 200 g to 280 g

Preparations of experiment: A rat is fasted 12 hours before the experiment. After the rat is anesthetized by intraperitoneal administration of nenbutal, the stomach is shaved with an electric razor, cleaned with ether, and cut open. The abdominal aorta upper the renal artery is clamped. The UW solution is adapted to be perfused from the abdominal aorta under the renal artery.

Grouping: Control group: UW solution only, D-allose group: D-allose is added to the UW solution at a concentration of 5 mg/ml.

Experimental method: In the control group and the D-allose group, the kidney is withdrawn after perfusion of the UW solution in each group, put in the UW solution of each of the control group and the D-allose group, and preserved at 4° C. in pre or for 12, 24, 48 or 72 hours.

Estimation: Expression of detrimental factor ICAM-1 and regeneration factor EGF in mRNA was examined by northern blot.

2.

Object: male rats with a body weight of 200~250 g Experimental method: After anesthetization of a rat with nenbutal, a renal ischemic model is prepared.

Renal ischemic model: After extraction of the right kidney, the left kidney blood vessel is clamped for 45 minutes.

400 mg/kg of the solution is intravenously administered to the D-allose group 30 minutes before the renal ischemia. A raw feed is administered to the control group.

Estimation: Change with time of a CINC-1 protein amount and MPO as an index of accumulation of leukocytes after ischemic reperfusion

[Results]

1. The effect of the allose-containing UW solution on the ICAM-1 mRNA expression is shown in FIG. 10.

The expression of 1CAM-1 mRNA during the kidney preservation is gradually increased in the control group, and reaches the maximum level after 24 hours. Meanwhile, the expression is reduced in the D-allose group, which is clearly observed after 12 hours and 24 hours in particular.

The effect of the allose-containing UW solution on the EGF mRNA expression is shown in FIG. 11.

The expression of EGF mRNA in the control group is decreased with the lapse of the preservation time which shows the decrease of the regeneration factor, whereas the expression in the D-allose group is still maintained in 48 hours and 78 hours.

2. The CINC-1 protein amount after ischemic reperfusion reaches the peak after 2 hours and then decreased, but it is significantly decreased in the pre-administration of allose (FIG. 12).

MPO as the index of accumulation of leukocytes reaches the peak after 6 hours of reperfusion, but is inhibited with allose (FIG. 13).

[Considerations]

The foregoing results have suggested a possibility that when D-allose is added to the UW solution, the expression of ICAM-1 as the bonding factor that causes the functional disorder of the transplanted kidney after renal transplantation is inhibited to maintain the expression of EGF that acts on regeneration of the kidney. The results have further suggested a possibility that the production of CINC-1 after ischemic reperfusion in the same condition as after transplantation is inhibited to reduce the accumulation of leukocytes in the kidney by the inhibition of MPO.

D-allose has proved to have the antioxidation activity (Murata et al., J. Bioengineering and Bioscience, 2003). The results that this activity is effective for preservation of culture cells, sperms or the like have been also obtained. It has been considered well that this activity leads to an activity of protecting the transplanted kidney from the functional disorder.

In addition, the foregoing activity has been confirmed. Thus, there is a possibility of using D-allose as a more effective preservative solution.

From now on, it is required to examine the addition amount of D-allose, to confirm effectiveness of ICAM-1 and EGF at protein levels and to estimate the renal function after transplantation with BUN, Cr and the like. The present inventors have already proved that the pre-administration of D-allose inhibits the activation and the floating of neutrophils after ischemic reperfusion of the rat kidney and decreases the functional disorder of the kidney (WO 03/097820).

Along with these results, it is finally considered that in addition to the improvement of the preservative solution in renal transplantation, D-allose is administered before withdrawal of the kidney for transplantation, and the kidney is thereafter withdrawn and preserved with the D-allose-containing preservative solution. Further, it has been suggested that the functional disorder and the rejection of the kidney after transplantation can be prevented by continuously administering D-allose also after transplantation. It is thus intended to establish such a new system of renal transplantation with D-allose.

The effects of D-allose observed in the kidney are considered to be likewise applied to other organs (liver, heart, lung and the like).

Example 4

At present, 10% to 15% of couples who want to have a child are fertile. Recent introduction of the assisted reproductive technology (ART) makes it possible for couples so far considered absolutely fertile to have a child, which helps to improve QOL of patients. Among others, when a man of reproductive age experiences anticancer chemotherapy or orchidectomy, a case of long-term freeze-preservation of sperms has been increased for hoping to have a child in future, and the further improvement of the preservative solution has been in demand.

A report stating that oxidative stress affects a survival rate and a movement rate of sperms has been lately found in various documents, attracting much interest.

In this Example, the present inventors improved a freeze-preservative solution for sperms using D-allose having an antioxidation activity among the rare sugars, and examined the results thereof.

[Method]

Semens of ten healthy men who were 24 to 44 years old (mean: 29.9) with normal semens were used.

Consent was obtained from all subjects, and a uniform semen sampling method was conducted.

The semen was manually collected after abstinence for 3 to 5 days, liquefied at room temperature, and then washed and concentrated by a 80% Percoll liquid agitation density gradient method. The resulting sperm turbid solution (0.2 ml) and the freeze-preservative solution were mixed in equal amounts, and the mixture was charged into a freezing tube (serum tube, Sumitomo Bakelite), frozen by a liquid nitrogen vapor freezing method, and then preserved in a liquid nitrogen tank. The freeze-preservative solution (refer to FIG. 14) was used such that the mixing amounts of D-allose and D-glucose were changed (A group=1:0, B group=3:1, C group=1:1, D group=1:3, E group=0:1) without changing the number of moles of the sugar in a KS-II sperm preservative solution. One month later, the frozen sperms were thawed in warm water (30° C.) with shaking. Further, for removal of the freeze-preservative solution and reconcentration, the density gradient centrifugation method was conducted, and the resulting sperm floating solution was examined.

As the examination method, the sperm movement rate was measured by a visual observation method with Makler Counting Chamber and C-IMAGING SYSTEMS, and the survival rate was measured by 0.5% Eosin Y dying.

The sperm freezing method was shown in FIG. 15. First, liquid sperms were subjected to an agitation density gradient method using 80% Percoll solution to obtain washed and concentrated sperms. Subsequently, the sperms were mixed with the sperm preservative solution, and the preserved sperms were frozen by a liquid nitrogen vapor freezing method, and then preserved in a liquid nitrogen tank for 1 month. Soon after thawing, the sperms were diluted with a Hanks solution, and the removal of the preservative solution and the reconcentration were conducted by the agitation density gradient method using 80% Percoll solution.

[Results]

1) Since the measurement with C-IMAGING SYSTEMS is influenced by the density of sperms, impurities, temperatures and the like and lacks reproducibility, the results obtained by visual observation were this time shown.

2) With respect to one of ten specimens, the results were not obtained because the serum tube was broken.

3) The freeze-preservative solution using D-allose alone was high in movement rate of thawed sperms in the eight of nine cases in comparison with the existing KS-II preservative solution using glucose only. (Refer to FIG. 16, P=0.0469, Mann-Whitney U-test).

4) The freeze-preservative solution using D-allose did not show a clear effect in the survival rate (refer to FIG. 17).

[Considerations]

1) There is a high possibility that the physiological activity of D-allose usefully acts to improve the movement rate of thawed sperms.

2) There is a need to study in future the physiological activity of D-allose and the functional system on sperms.

3) First, an experimental system of observing the change in sperm movement rate with time using the sperm culture solution containing D-allose is established and practiced.

4) The same experiments are studied on ova also.

5) Preservation experiments are conducted using animal sperms, ova and fermented ova.

6) As confirmed in Example 2, the effect of cell freeze-preservation is high in the high concentration region of D-allose. The analysis using D-allose at a high concentration is required in the preservation of sperms also.

INDUSTRIAL APPLICABILITY

The kidney is one of organs with the highest oxidative stress in the living body. The importance of radical damage has been long pointed out in which active oxygen and free radical are involved in triggering and progression systems of various renal diseases such as acute renal insufficiency, drug-induced renal disorder, glomerulonephritis, diabetic nephropathy, chronic renal insufficiency and renal transplantation. However, the effect of the antioxidative agent against the renal diseases has not yet been sufficiently clarified. In the prevention and therapy of the various renal diseases and the preservation of organs, compounds useful in therapy and prevention of the renal diseases and as an organ preservative agent have been demanded. Meanwhile, it is considered that the rare sugars have the activity of inhibiting production of active oxygen and the activity of eliminating active oxygen and are effective for coping with active oxygen generated in long-term preservation of cells or organs in an ischemic condition. When using this quality, a preservative solution effective for cells can be developed, and a new renal transplantation system using D-allose can be established.

The present inventors have already observed the activity of protection from ischemic disorder in other organs such as the liver, heart and skin. The application of D-allose to the preservative agent of not only the kidney but also many organs can be expected.

At present, 10% to 15% of couples who want to have a child are fertile. Recent introduction of the assisted reproductive technology (ART) makes it possible for couples so far considered absolutely fertile to have a child, which helps to improve QOL of patients. In this therapy, the freeze-preservation of sperms or ova is indispensable, and the development of a method that allows long-term freeze-preservation while satisfactorily maintaining the function thereof is considered to provide a great merit in the therapy. In animals, especially domestic animals such as cattle or fish, the freeze-preservation of sperms, ova and fermented ova has been generally conducted widely, and it can be an important method in this field as well.

Moreover, the freeze-preservation of not only sperms, but also ova and fermented ova has become important. There is a possibility of developing an effective preservative solution for them.

Figure 1:
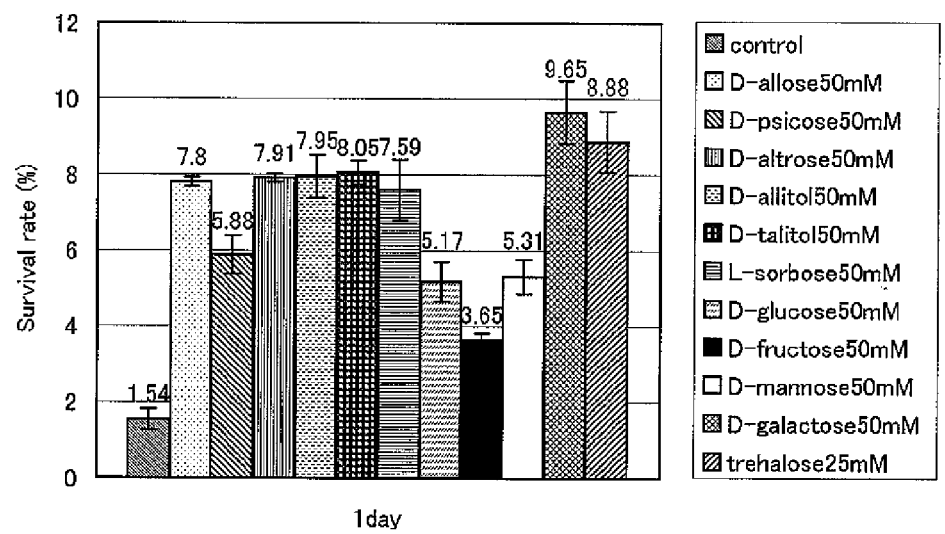
FIG. 1 It is a graph showing comparison of the survival rate after thawing HFB cells.
Figure 2:
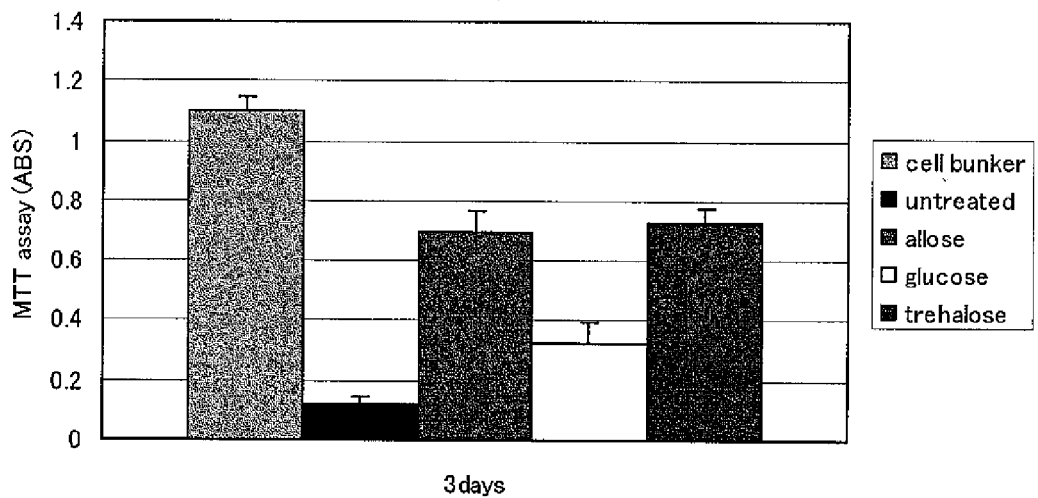
FIG. 2 It is a graph showing comparison of growth ability after thawing HFB cells.
Figure 3:
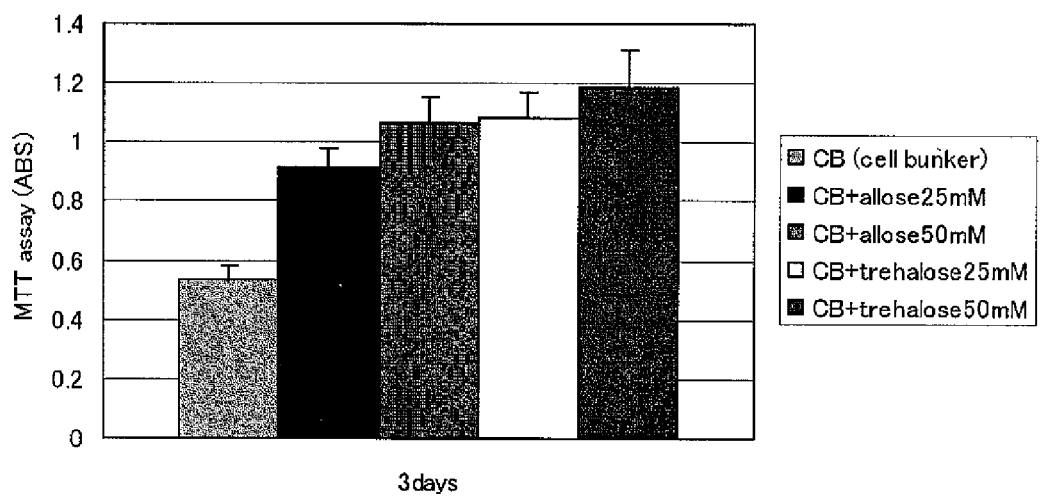
FIG. 3 It is a graph showing comparison of growth ability after thawing NIH 3T3 cells.
Figure 4:
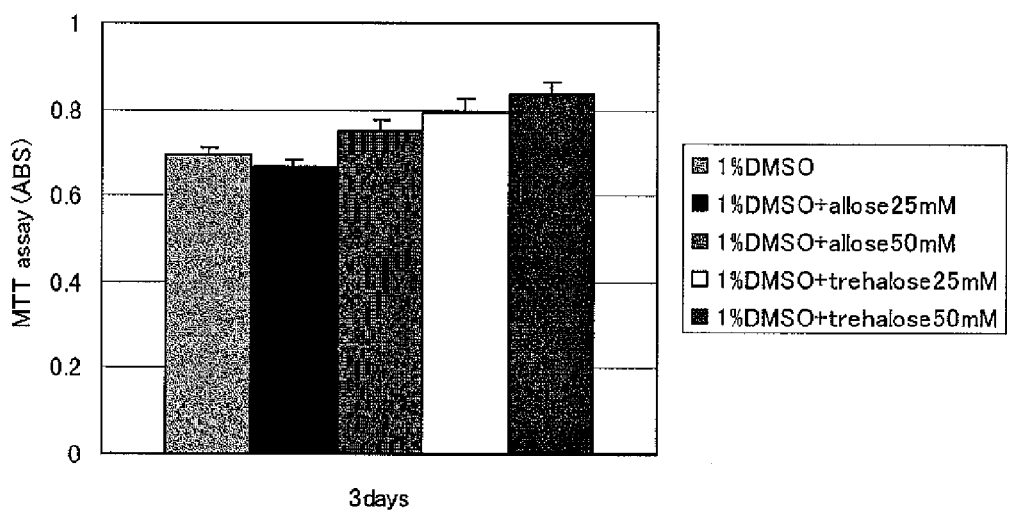
FIG. 4 It is a graph showing comparison of growth ability after thawing HFB cells.
Figure 5:
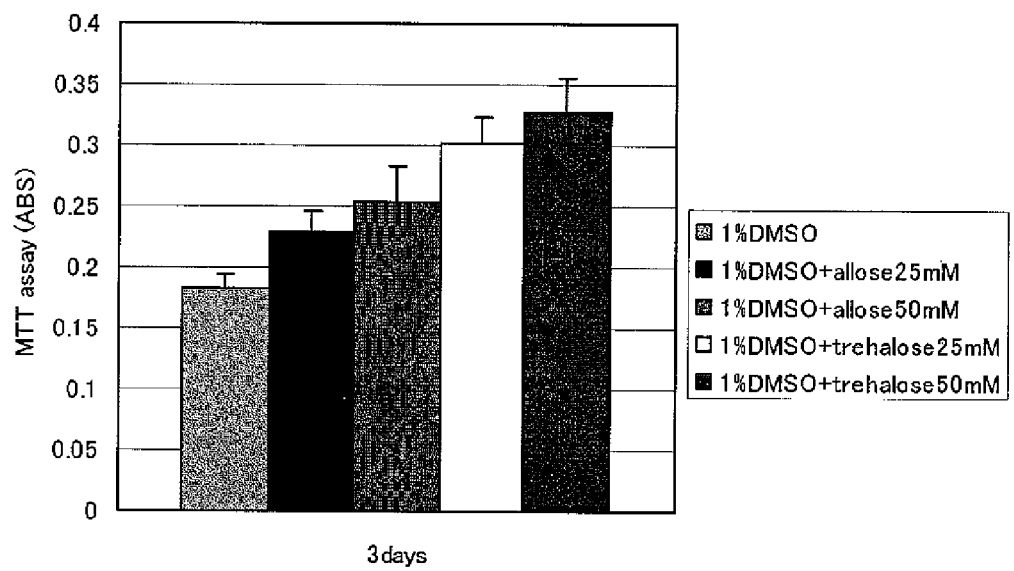
FIG. 5 It is a graph showing comparison of growth ability after thawing OVCAR-3 cells.
Figure 6:
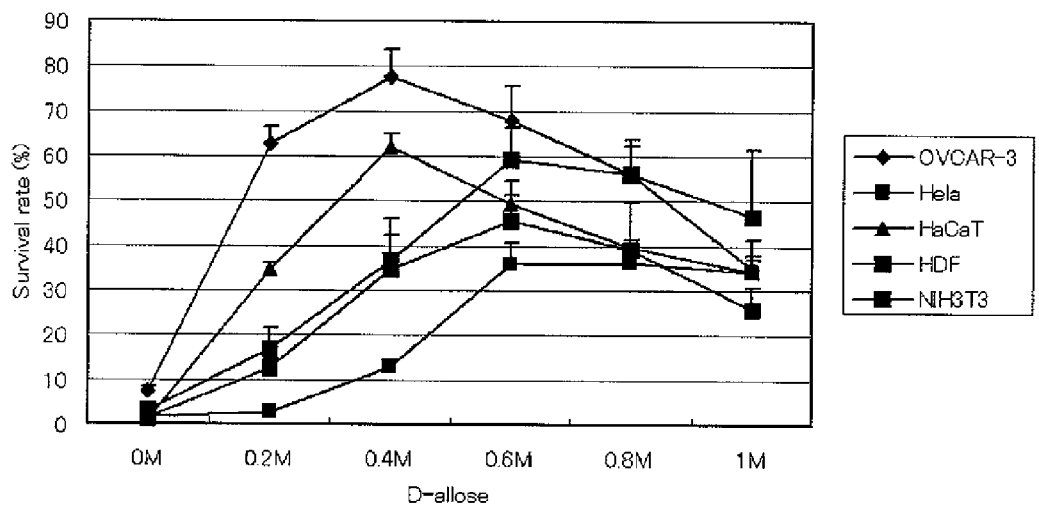
FIG. 6 It is a graph showing the relation between concentration of D-allose and cell survival rate.
Figure 7:
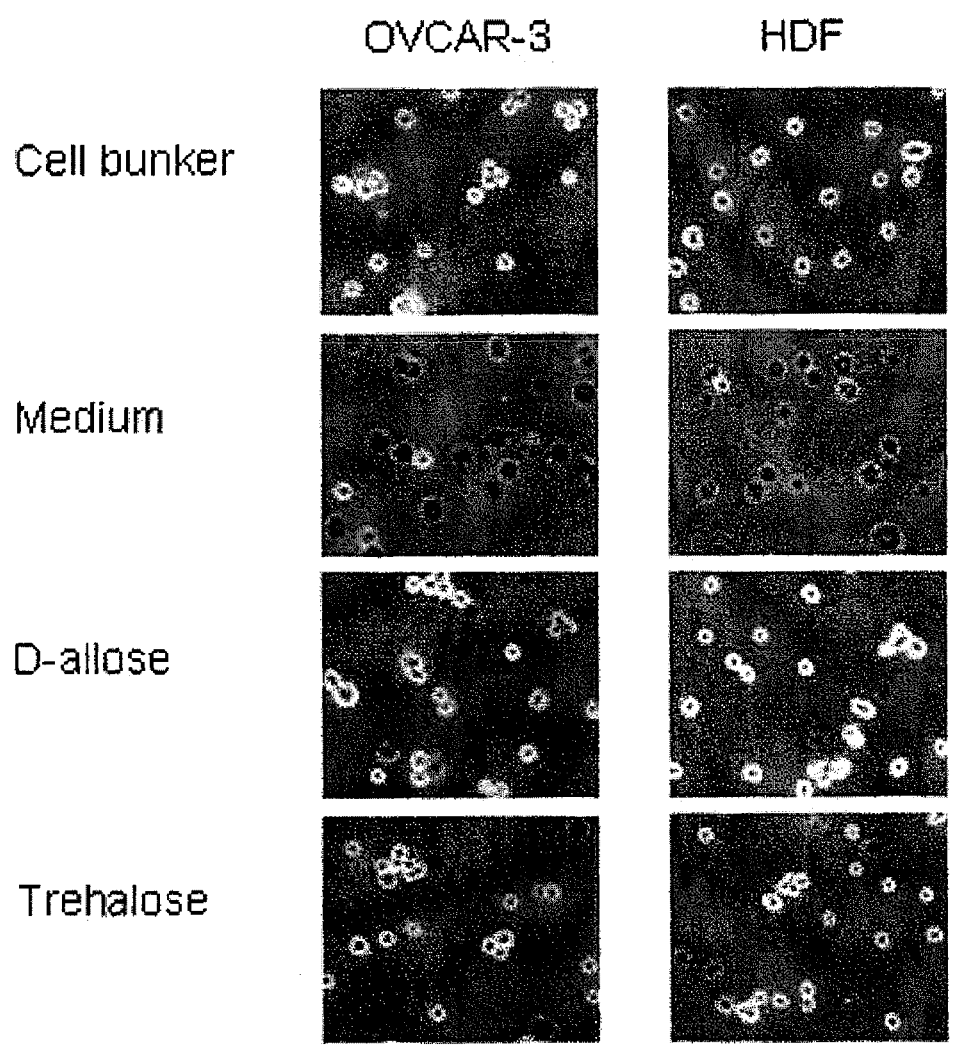
FIG. 7 It is a view showing estimation of cell survival by trypan blue dying method.
Figure 8:
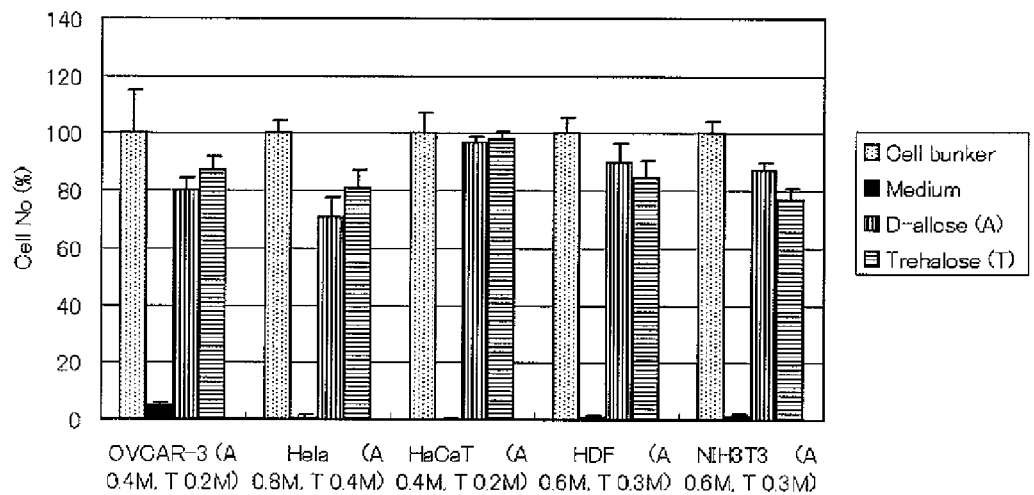
FIG. 8 It is a graph showing comparison of growth ability after thawing cells.
Figure 9:
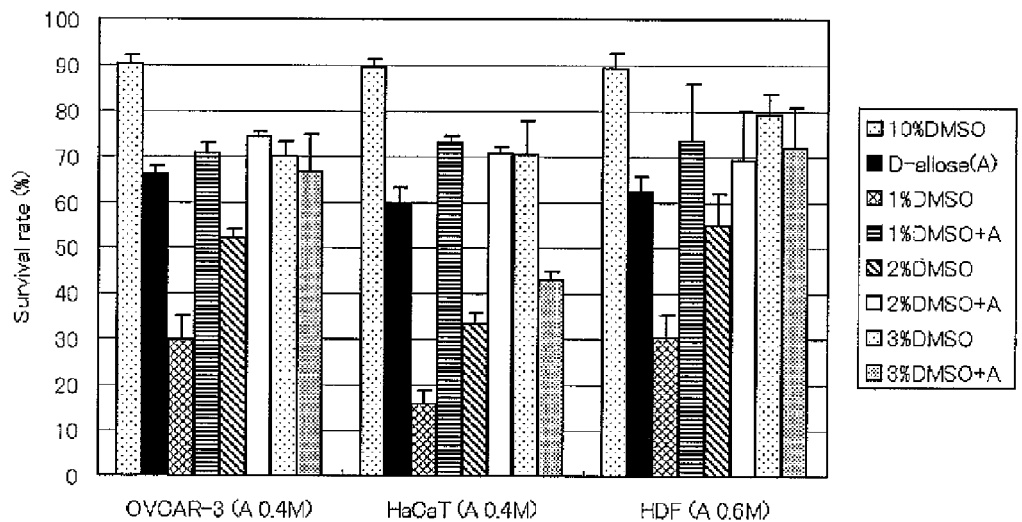
FIG. 9 It is a graph showing results of studying cell survival rate in the combination of D-allose and DMSO at a low concentration.
Figure 10:
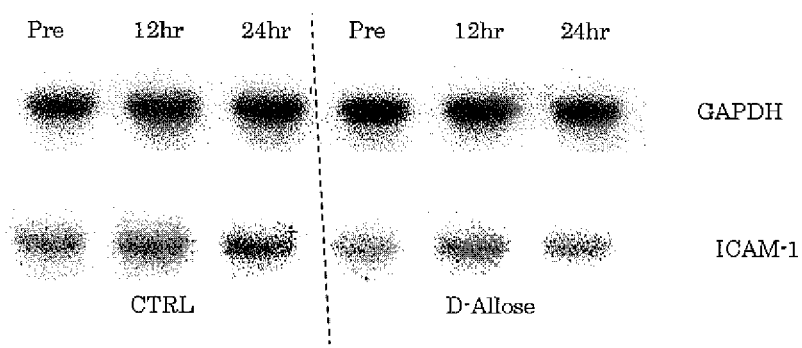
FIG. 10 It is a view showing an effect of an allose-containing UW solution on ICAM-1 mRNA expression.
Figure 11:
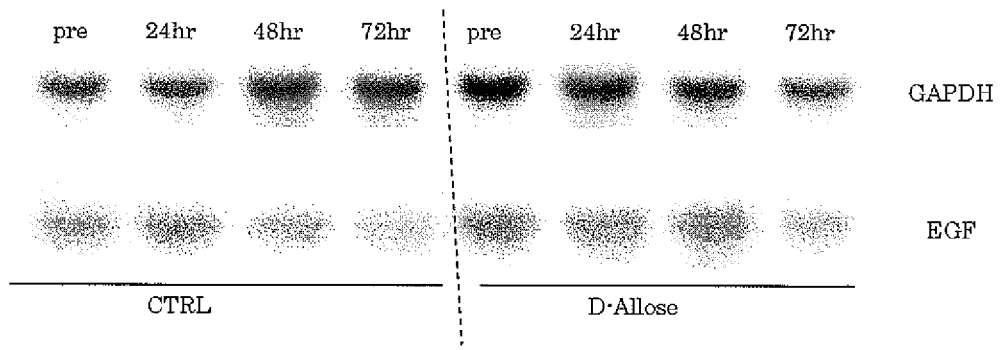
FIG. 11 It is a view showing an effect of an allose-containing UW solution on EGF mRNA expression.
Figure 12:
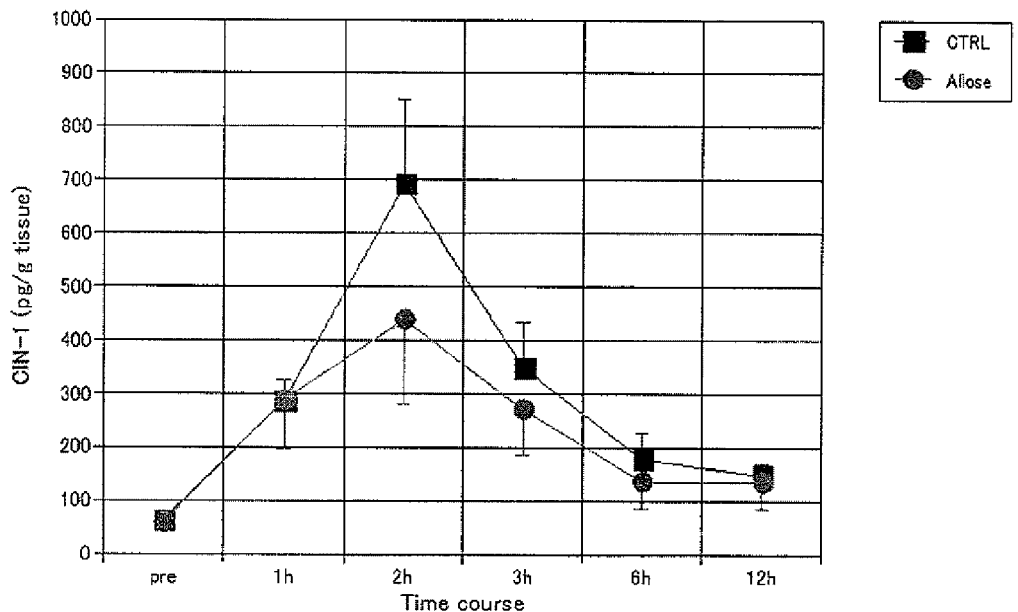
FIG. 12 It is a view showing an effect of an allose-containing UW solution on an expression amount of CINC-1.
Figure 13:
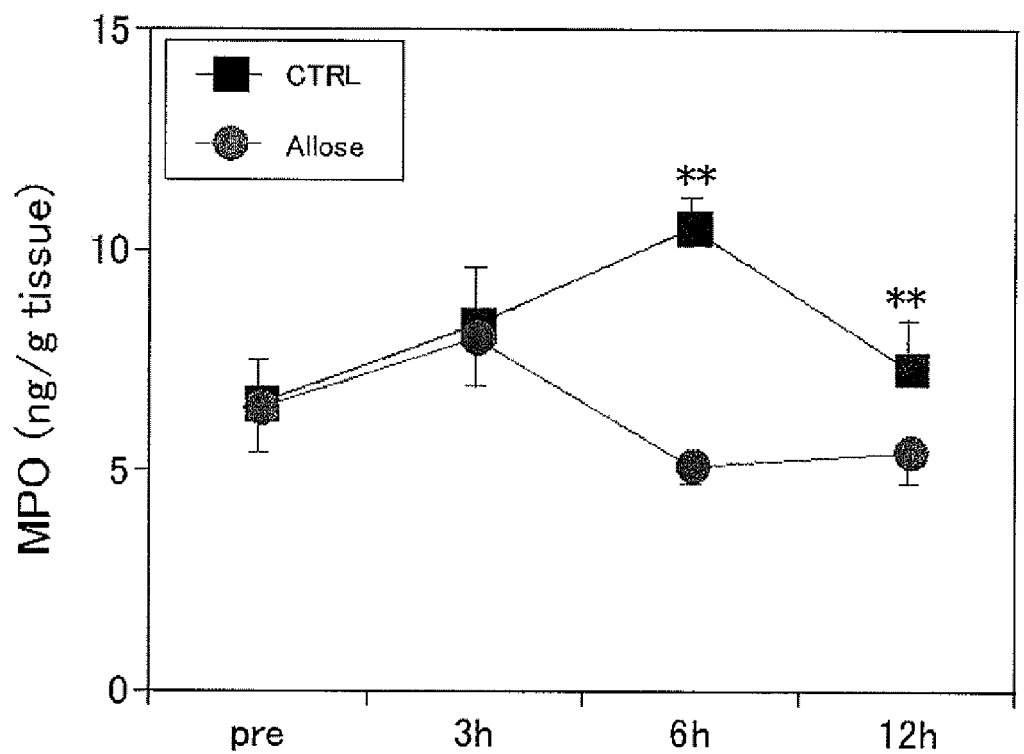
FIG. 13 It is a graph showing an effect of an allose-containing UW solution on leukocyte accumulation in the kidney.
Figures 14, 15:
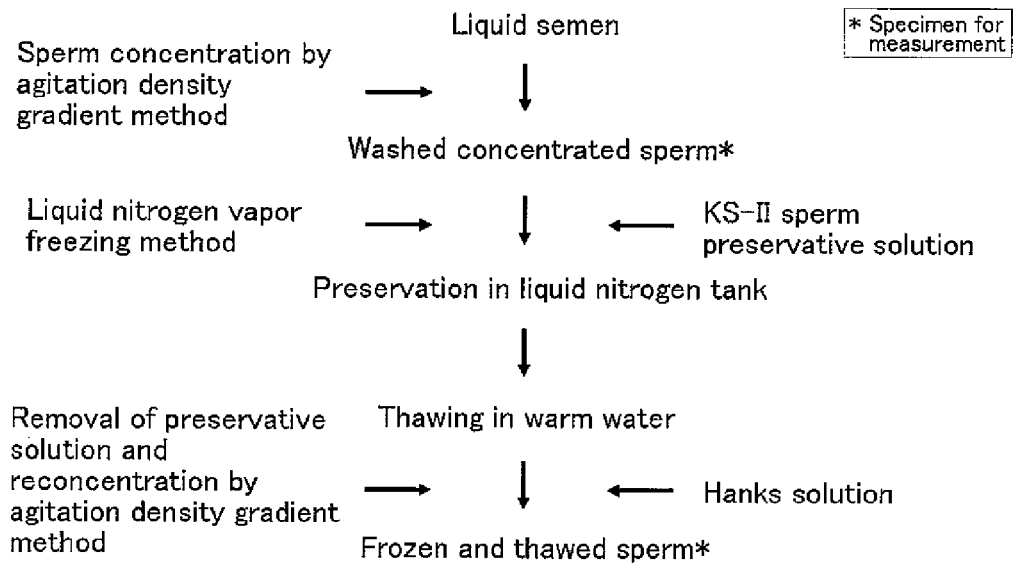
FIG. 14 It is a view showing a composition of a KS-II sperm preservative solution (D-glucose is replaced with D-allose).
FIG. 15 It is a view showing a sperm freezing method.
Figure 16:
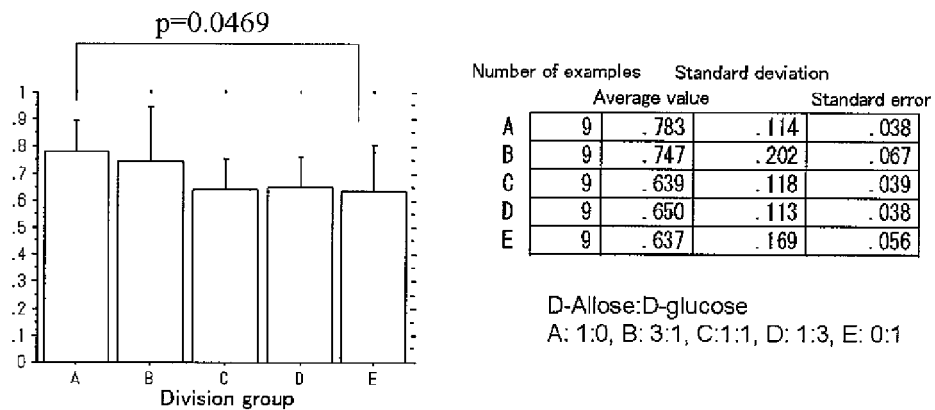
FIG. 16 It is a view showing a movement rate of frozen and thawed sperms using a freeze-preservative solution containing D-allose.
Figure 17:
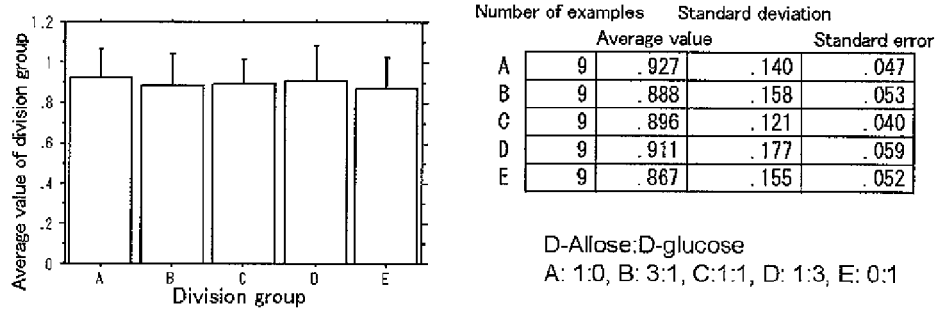
FIG. 17 It is a view showing a survival rate of frozen and thawed sperms using a freeze-preservative solution containing D-allose.
Figure 18:
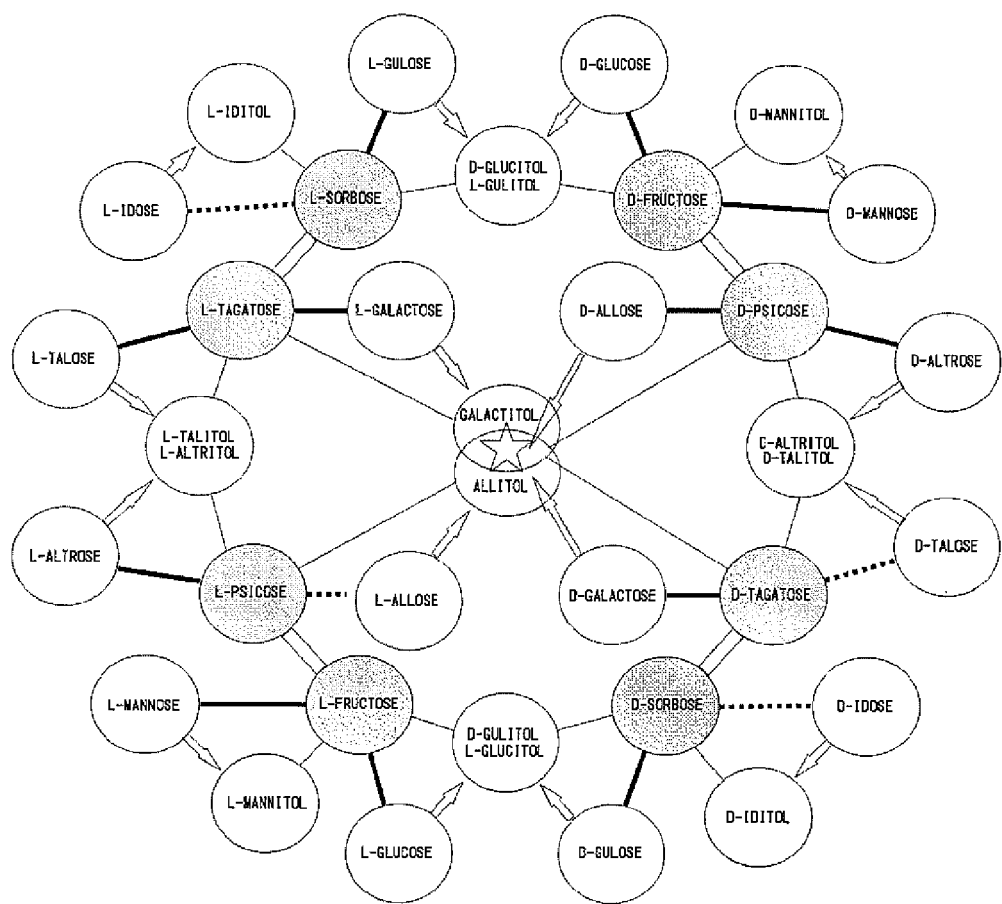
FIG. 18 It is an explanatory view of Izumoring C6 in a lower portion of FIG. 19.
Figure 19:
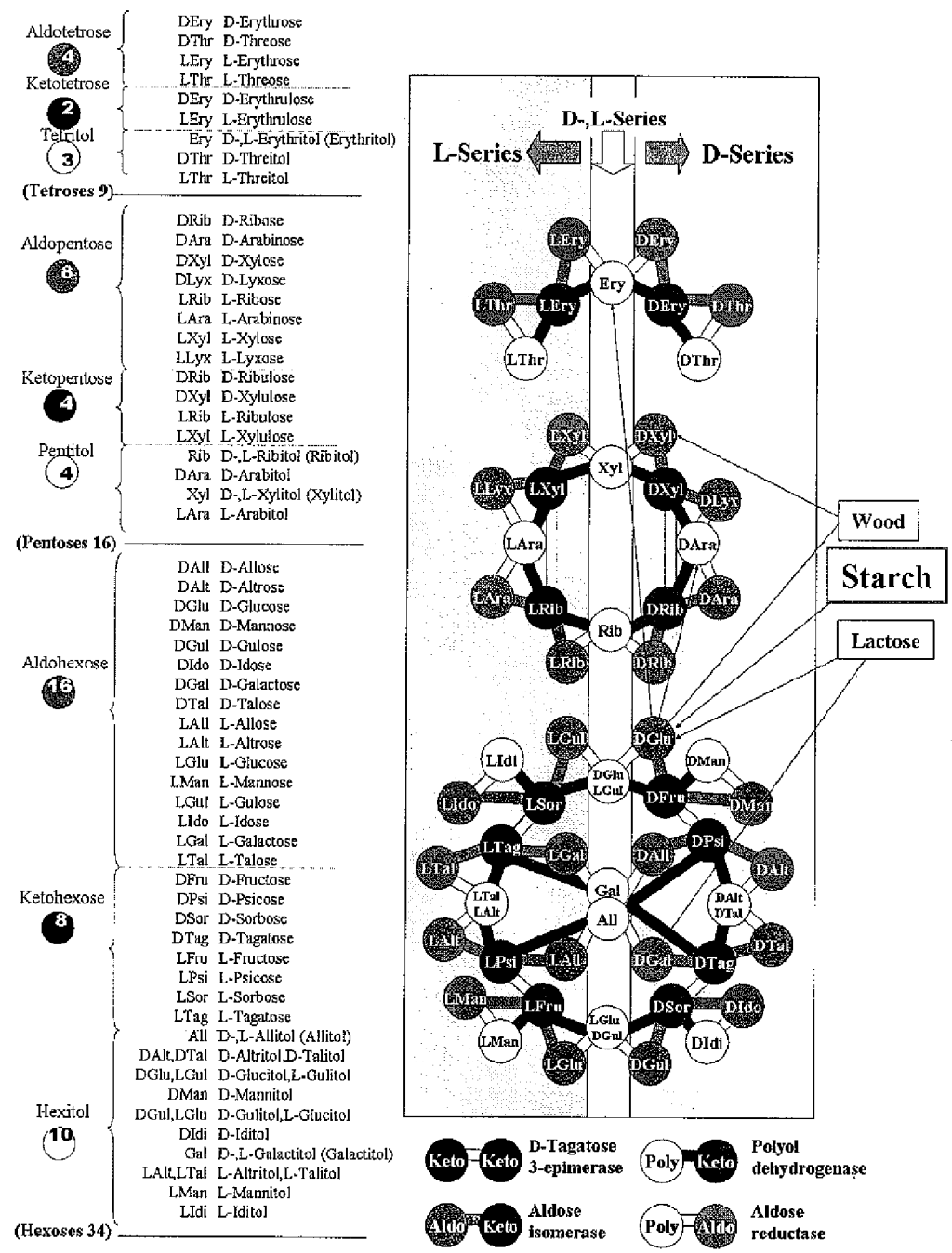
FIG. 19 It is an Izumoring link view.

The invention claimed is:

1. A preservative solution for low temperature preservation of animal or human organs and animal or plant tissues or cells, wherein the solution is a University of Wisconsin solution containing 0.4M to 0.6M of D-allose.

2. A method for low temperature preservation of an animal or human organ or an animal or plant tissue at a low temperature, which comprises (a) contacting the organ or the tissue with a preservative solution containing 0.4M to 0.6M of D-allose for low temperature preservation, and (b) cooling the organ or the tissue being contacted with the preservative solution to a low temperature of from −5 to 20° C.

3. The method according to claim 2, which preserves a human kidney.

4. A method for low temperature preservation of a human or animal cell at a low temperature, which comprises (a) contacting the cell with a preservative solution containing 0.4M to 0.6M of D-allose for low temperature preservation, and (b) cooling the cell being contacted with the preservative solution to a low temperature of from −5 to 20° C.

5. The method according to claim 4, which preserves a sperm or ovum.

6. The method according to claim 4, which preserves a fermented ovum.

7. A method for low temperature preservation of an animal or human organ or an animal or plant tissue at a low temperature, which comprises (a) contacting the organ or the tissue with a preservative solution containing 0.4M to 0.6M of D-allose for low temperature preservation, and (b) cooling the organ or the tissue being contacted with the preservative solution to a low temperature of from 20° C. to −196° C.

8. The method according to claim 7, which preserves a human kidney.

9. A method for low temperature preservation of a human or animal cell at a low temperature, which comprises (a) contacting the cell with a preservative solution containing 0.4M to 0.6M of D-allose for low temperature preservation, and (b) cooling the cell being contacted with the preservative solution to a low temperature of from 20° C. to −196° C.

10. The method according to claim 9, which preserves a sperm or ovum.

11. The method according to claim 9, which preserves a fermented ovum.

* * * * *